US010759801B2

(12) United States Patent
Lourenço et al.

(10) Patent No.: US 10,759,801 B2
(45) Date of Patent: Sep. 1, 2020

(54) PROCESS FOR THE PREPARATION OF UMECLIDINIUM BROMIDE (71) Applicant: Hovione Scientia Limited, Cork (IE)

(72) Inventors: Nuno Torres Lourenço, Lisbon (PT); Luis Sobral, Loures (PT); Rafael Antunes, Setúbal (PT); Maria Santos, Lisbon (PT); Margarida Espadinha, Mem Martins (PT)

(73) Assignee: Hovione Scientia Limited, Cork (IE)

( * ) Notice: Subject to any disclaimer, the term of this patent is extended or adjusted under 35 U.S.C. 154(b) by 0 days.

(21) Appl. No.: 16/349,404

(22) PCT Filed: Nov. 10, 2017

(86) PCT No.: PCT/GB2017/053396
§ 371 (c)(1),
(2) Date: May 13, 2019

(87) PCT Pub. No.: WO2018/087561
PCT Pub. Date: May 17, 2018

(65) Prior Publication Data
US 2019/0263814 A1    Aug. 29, 2019

(30) Foreign Application Priority Data
Nov. 14, 2016 (PT) .......................... 109740

(51) Int. Cl.
| C07D 471/08 | (2006.01) |
| A61K 9/00 | (2006.01) |
| A61K 9/14 | (2006.01) |
| C07D 211/62 | (2006.01) |
| C07D 453/02 | (2006.01) |

(52) U.S. Cl.
CPC .......... *C07D 471/08* (2013.01); *A61K 9/0075* (2013.01); *A61K 9/14* (2013.01); *C07D 211/62* (2013.01); *C07D 453/02* (2013.01); *C07B 2200/13* (2013.01)

(58) Field of Classification Search
CPC .................................................. C07D 471/08
USPC ....................................................... 546/133
See application file for complete search history.

(56) References Cited

U.S. PATENT DOCUMENTS

| 6,103,725 | A * | 8/2000 | Kennis | .................. | C07D 263/58 |
| | | | | | 514/254.02 |
| 7,488,827 | B2 * | 2/2009 | Laine | .................... | C07D 453/02 |
| | | | | | 546/133 |
| 9,273,001 | B2 | 3/2016 | Strachan | | |
| 9,657,011 | B2 * | 5/2017 | Hossner | ................ | C07D 211/62 |
| 2006/0223792 | A1 * | 10/2006 | Butler | .................... | A61K 31/135 |
| | | | | | 514/217.11 |

FOREIGN PATENT DOCUMENTS

| CN | 105461710 A | 4/2016 | |
| PT | 109740 | 11/2016 | |
| WO | WO 99/06387 | * 2/1999 | ........... C07D 307/79 |
| WO | 2005104745 A2 | 11/2005 | |
| WO | 2011029896 A1 | 3/2011 | |
| WO | 2014027045 A1 | 2/2014 | |

(Continued)

OTHER PUBLICATIONS

Jerry March, Advanced Organic Chemistry: Reactions, Mechanisms, and Structure, 1992 p. 411.*
Foreign communication from a related application—International Search Report and Written Opinion of the International Searching Authority of International Application No. PCT/GB2017/053396 dated Jan. 3, 2018, 17 pages.
Foreign communication from a related application—International Preliminary Report on Patentability of International Application No. PCT/GB2017/053396 dated Feb. 25, 2019, 17 pages.

(Continued)

*Primary Examiner* — Nizal S Chandrakumar
(74) *Attorney, Agent, or Firm* — Conley Rose, P.C.; Rodney B. Carroll (57) ABSTRACT The present invention discloses processes comprising a) reacting ethyl isonipecotate with 1-bromo-2-chloroethane in the presence of an organic base in a solvent to form ethyl 1-(2-chloroethyl)piperidine-4-carboxylate (II) or a salt thereof. Process step a) may be included in a process for preparing umeclidinium bromide that comprises further process steps: b) reacting ethyl 1-(2-chloroethyl)piperidine-4-carboxylate (II) or a salt thereof with lithium diisopropylamide in a solvent to form ethyl 1-azabicyclo[2.2.2]octane-4-carboxylate (III); c) reacting ethyl 1-azabicyclo[2.2.2]octane-4-carboxylate (III) with phenyl lithium in a solvent to form 1-azabicyclo[2.2.2]oct-4-yl(diphenyl)methanol (IV); and d) reacting 1-azabicyclo[2.2.2]oct-4-yl(diphenyl)methanol (IV) with ((2-bromoethoxy)methyl) benzene in a solvent to form 4-[hydroxyl(diphenyl)methyl]-1-[2-(phenylmethyl)oxy]ethyl]-1-azoniabicyclo[2.2.2]octane bromide (I), umeclidinium bromide. A process comprising d) reacting 1-azabicyclo[2.2.2]oct-4-yl(diphenyl)methanol with ((2-bromoethoxy)methyl) benzene in a solvent to form 4-[hydroxyl(diphenyl)methyl]-1-[2-(phenylmethyl)oxy]ethyl]-1-azoniabicyclo[2.2.2]octane bromide (I), umeclidinium bromide, wherein the solvent is selected from cyclic ethers such as tetrahydrofuran, aromatic solvents, such as toluene, ketones such as acetone and protic solvents such as water or combinations thereof, optionally wherein the solvent is water is also disclosed. Umeclidinium bromide obtainable from the disclosed processes, ethyl 1-(2-chloroethyl)piperidine-4-carboxylate (II) and pharmaceutical compositions are also disclosed.

19 Claims, 7 Drawing Sheets

(56) References Cited

FOREIGN PATENT DOCUMENTS

WO      2016071792  A1      5/2016
WO      2018087561  A1      5/2018

OTHER PUBLICATIONS

Foreign communication from a related application—Search Report of Portuguese Patent Application No. 109740 dated May 26, 2017, with English translation, 7 pages.

Flick, Andrew C., et al., "Synthetic approaches to the 2014 new drugs," Bioorganic & Medicinal Chemistry, 2016, pp. 1937-1980, vol. 24, Elsevier Ltd.

Qiao, Hongwen, et al., "Synthesis and evaluation of novel tropane derivatives as potential PET imaging agents for the dopamine transporter," Bioorg Med Chem Lett., Jul. 1, 2012, pp. 4303-4306, vol. 22, Issue No. 13, Elsevier Ltd.

\* cited by examiner

Peak Results

|   | RT | FRT | Name | Area | % Area | SIGNAL NOISE |
|---|---|---|---|---|---|---|
| 1 | 11.620 | | | 6813860 | 99.30 | 43.6 |
| 2 | 14.568 | | | 3516 | 0.05 | 0.0 |
| 3 | 17.764 | | | 15448 | 0.23 | 0.2 |
| 4 | 17.982 | | | 6094 | 0.09 | 0.1 |
| 5 | 18.354 | | | 5670 | 0.08 | 0.1 |
| 6 | 29.467 | | | 13629 | 0.20 | 0.1 |
| 7 | 31.012 | | | 3336 | 0.05 | 0.0 |
| Sum | | | | 6861553 | | |

FIG. 5

Peak Results

|   | RT | FRT | Name | Area | % Area | SIGNAL NOISE |
|---|---|---|---|---|---|---|
| 1 | 10.080 |  |  | 880 | 0.02 | 0.0 |
| 2 | 16.912 |  |  | 7998 | 0.16 | 0.1 |
| 3 | 18.581 |  |  | 1916 | 0.04 | 0.0 |
| 4 | 19.080 |  |  | 5017807 | 99.27 | 39.5 |
| 5 | 23.186 |  |  | 1316 | 0.03 | 0.0 |
| 6 | 23.504 |  |  | 13126 | 0.26 | 0.1 |
| 7 | 23.686 |  |  | 5607 | 0.11 | 0.1 |
| 8 | 25.634 |  |  | 6073 | 0.12 | 0.0 |
| Sum |  |  |  | 5054725 |  |  |

PROCESS FOR THE PREPARATION OF UMECLIDINIUM BROMIDE

CROSS REFERENCE TO RELATED APPLICATIONS

This application is a filing under 35 U.S.C. 371 of International Application No. PCT/GB2017/053396 filed Nov. 10, 2017, entitled "Process for the Preparation of Umeclidinium Bromide" which claims priority to Portuguese Patent Application No. 109740 filed Nov. 14, 2016, which applications are incorporated by reference herein in their entirety.

FIELD OF INVENTION

The present invention relates to novel processes for the preparation of 4-[hydroxyl(diphenyl)methyl]-1-[2-(phenylmethyl)oxy]ethyl]-1-azoniabicyclo[2.2.2]octane bromide, a compound known by the name umeclidinium bromide.

Umeclidinium bromide is an effective anticholinergic agent and has been used in the treatment of respiratory diseases such as asthma or chronic obstructive pulmonary disease (COPD). It is used for preparing pharmaceutical compositions to be administrated as a dry powder for oral inhalation at once-daily micrograms dose. New compositions, combinations, forms of administration (e.g. metered-dose inhalers) and dosages using umeclidinium bromide are being developed.

BACKGROUND OF THE INVENTION

The compound umeclidinium bromide of molecular structure (I) depicted below is a long-acting muscarinic antagonist used in the treatment of airflow obstruction in patients with chronic obstructive pulmonary disease (COPD), including chronic bronchitis and emphysema.

(I)

The synthesis of umeclidinium bromide has been claimed in WO2005/104745 involving four steps as follows:

ethyl 1-(2-chloroethyl) piperidine-4-carboxylate
(II)

(III)

(IV)

(I)
Umeclidinium Bromide

The key intermediate ethyl 1-(2-chloroethyl)piperidine-4-carboxylate of formula (II) is synthesized by reacting 1-bromo-2-chloroethane and ethyl isonipecotate in the presence of potassium carbonate in acetone. However, the compound of formula (II) is prepared in very low yields (39%), due to the formation of a dimer by-product, diethyl 1,1'-(ethane-1,2-diyl) bis(piperidine-4-carboxylate) (V), which must be separated from the primary compound by chromatographic techniques.

diethyl 1,1'-(ethane-1,2-diyl)bis(piperidine-4-carboxylate)

In order to overcome the dimerization issue and consequent low yields, WO2014/027045 claims an alternative two-step process for the preparation of the compound of formula (II) in better yield (80%) as follows:

ethyl 1-(2-chloroethyl)
piperidine-4-carboxylate

There is no doubt that such synthetic alternative can lead to better yields, but the need for two reaction steps, instead of a single one as described in WO2005/104745, is not the best solution for an industrial application. Additionally, WO2014/027045 discloses the use of a high temperature in the first step and the use of a highly corrosive and toxic reagent in the second step, namely thionyl chloride that produces environmentally unfriendly SOx by-products. Three major disadvantages when compared to the mild conditions described in WO2005/104745.

Alternatively, WO2016/071792 claims a one-step process for the preparation of compound of formula (II) which comprises the reaction of ethyl isonipecotate with halogenated-acetaldehyde in a mixture of methanol:acetic acid together with a reducing agent as follows:

ethyl 1-(2-chloroethyl)
piperidine-4-carboxylate

Although leading to better yields (90%) in comparison to those described in WO2005/104745 and WO2014/027045, the synthesis requires the use of methanolic-aqueous acidic solutions, which can degrade the ester moiety to some extent, prior to the reaction with the reductive agents.

WO2011/029896 describes an alternative process to prepare umeclidinium bromide through the use of different intermediates as follows:

-continued wherein P is a protecting group; R is selected from the group consisting of alkyl, alkenyl, alkynyl, cycloalkyl, cycloalkenyl, heterocycle, aryl and heteroaryl; and X and Y are leaving groups, provided that X and Y are different.

However, this process is more complex than the process disclosed in WO2005/104745 because it encompasses a longer synthetic route and includes extra protection-deprotection steps.

Unsolvated crystalline forms of umeclidinium bromide have been disclosed as polymorphs of the active pharmaceutical ingredient (WO2014/027045, U.S. Pat. No. 9,273,001 B2), showing that the compound may give rise to a variety of solids having distinct physical properties. The preparation of pure umeclidinium bromide in a single crystalline form has been a challenge for the industry as umeclidinium bromide is highly susceptible to forming solvates. Umeclidinium bromide solvates include a methanol solvate (CZ27764 (Sanofi)), and ethanol, 2-propanol, 2-methylpropan-1-ol, chlorobenzene and p-xylene solvates have been disclosed (WO2014/027045, U.S. Pat. No. 9,273,001 B2). 1-Propanol has been used as the solvent in the final process step to minimize solvate formation (U.S. Pat. No. 9,273,001 B2) avoiding the resuspension of the compound in ethyl acetate, methanol and water, which was previously required (example 84, Method B, WO2005/104745).

In order to fulfill the umeclidinium bromide market demand, there is a need to develop more efficient processes. Namely, processes that offer advantages over those previously disclosed in WO2016/071792, WO2005/104745, WO2014/027045 and WO2011/029896. There is also a need to provide processes that prepare umeclidinium bromide in a single, pure crystalline form with a consistent level of crystallinity and chemical purity.

SUMMARY OF THE INVENTION

According to one aspect of the present invention, there is provided a process for preparing umeclidinium bromide comprising:
a) reacting ethyl isonipecotate with 1-bromo-2-chloroethane in the presence of an organic base in a solvent to form ethyl 1-(2-chloroethyl)piperidine-4-carboxylate (II) or a salt thereof;
b) reacting ethyl 1-(2-chloroethyl)piperidine-4-carboxylate (II) or a salt thereof with lithium diisopropylamide in a solvent to form ethyl 1-azabicyclo[2.2.2]octane-4-carboxylate (III);
c) reacting ethyl 1-azabicyclo[2.2.2]octane-4-carboxylate (III) with phenyl lithium in a solvent to form 1-azabicyclo[2.2.2]oct-4-yl(diphenyl)methanol (IV); and
d) reacting 1-azabicyclo[2.2.2]oct-4-yl(diphenyl)methanol (IV) with ((2bromoethoxy)methyl) benzene in a solvent to form 4-[hydroxyl(diphenyl)methyl]-1-[2-(phenylmethyl) oxy]ethyl]-1-azoniabicyclo[2.2.2]octane bromide (I), umeclidinium bromide.

According to another aspect of the present invention, there is provided a process comprising:
a) reacting ethyl isonipecotate with 1-bromo-2-chloroethane in the presence of organic base in a solvent to form ethyl 1-(2-chloroethyl)piperidine-4-carboxylate (II) or a salt thereof.

According to a further aspect of the present invention, there is provided a process comprising:
d) reacting 1-azabicyclo[2.2.2]oct-4-yl(diphenyl)methanol with ((2-bromoethoxy)methyl) benzene in a solvent to form 4-[hydroxyl(diphenyl)methyl]-1-[2-(phenylmethyl) oxy]ethyl]-1-azoniabicyclo[2.2.2]octane bromide (I), umeclidinium bromide, wherein the solvent is selected from a group of cyclic ethers such as tetrahydrofuran, aromatic solvents, such as toluene, ketones such as acetone and protic solvents such as water or combinations thereof, optionally wherein the solvent is water.

Other aspects of the invention relate to ethyl 1-(2-chloroethyl)piperidine-4-carboxylate (II) and umeclidinium bromide obtainable by the processes of the present invention, and pharmaceutical compositions comprising said umeclidinium bromide.

Surprisingly, it has been found that step a) of the present invention affords the key intermediate ethyl 1-(2-chloroethyl)piperidine-4-carboxylate (II) in higher yields (66%) than the process disclosed in WO2005/104745 without needing to increase the number of process steps (such as protection-deprotection steps), without needing to use high temperatures and without needing to use undesirable reagents (such as corrosive reagents, toxic reagents or methanol/aqueous acidic systems). Step a) of the present invention controls the formation of undesirable by-products such as diethyl 1,1'-(ethane-1,2-diyl)bis(piperidine-4-carboxylate) (V). Ethyl 1-(2-chloroethyl)piperidine-4-carboxylate (II) obtained during step a) of the present invention can be either purified or used directly in the process steps that follow without purification (e.g. purification by chromatography). The processes of the present invention enable a telescoped (or one-pot) synthesis of umeclidinium bromide, whereby the starting material is subjected to successive chemical reactions. Such a synthesis is in great demand because it improves chemical reaction efficiency by avoiding separation and purification of intermediates, thereby saving time and resources whilst increasing chemical yield.

One advantage of step a) of the present invention is that use of the ethyl 1-(2-chloroethyl) piperidine-4-carboxylate (II) intermediate obtained from this process step allows the preparation of umeclidinium bromide in a single, pure crystalline form with a consistent level of crystallinity and chemical purity.

Additionally, it has been found that step d) of the present invention affords a product with a single, pure crystalline form with a consistent level of crystallinity and chemical purity. Therefore, one further advantage of the process of the present invention is that the umeclidinium bromide obtained during step d) of the present invention is a single, pure crystalline form with a consistent level of crystallinity and chemical purity.

Consequently, the present invention discloses processes for the preparation of umeclidinium bromide which afford a single, pure crystalline form with a consistent level of crystallinity and chemical purity.

Finally, the processes of the present invention enable the production of umeclidinium bromide with a particle size suitable for inhalation.

DETAILED DESCRIPTION OF THE INVENTION

The present invention provides alternative processes for preparing umeclidinium bromide and one of the key intermediates in preparing umeclidinium bromide, namely ethyl 1-(2-chloroethyl) piperidine-4-carboxylate (II).

The present invention may provide a process comprising the following steps:
a) reacting ethyl isonipecotate with 1-bromo-2-chloroethane in the presence of an organic base in a solvent to form ethyl 1-(2-chloroethyl)piperidine-4-carboxylate (II) or a salt thereof;
b) reacting ethyl 1-(2-chloroethyl)piperidine-4-carboxylate (II) or a salt thereof with lithium diisopropylamide in a solvent to form ethyl 1-azabicyclo[2.2.2]octane-4-carboxylate (III);
c) reacting ethyl 1-azabicyclo[2.2.2]octane-4-carboxylate (III) with phenyl lithium in a solvent to form 1-azabicyclo[2.2.2]oct-4-yl(diphenyl)methanol (IV);
d) reacting 1-azabicyclo[2.2.2]oct-4-yl(diphenyl)methanol (IV) with ((2-bromoethoxy) methyl) benzene in a solvent to form 4-[hydroxyl(diphenyl)methyl]-1-[2-(phenylmethyl) oxy]ethyl]-1-azoniabicyclo[2.2.2]octane bromide (I), umeclidinium bromide in a single, pure crystalline form and optionally;
e) recrystallizing umeclidinium bromide to consistently obtain a high purity product and optionally;
f) micronizing umeclidinium bromide to obtain a product with a particle size suitable for inhalation while maintaining its crystalline form.

Steps a) to e) may be combined in the absence of step f). Steps a) to d) and f) may be combined in the absence of step e).

Steps d) and e) may be combined in the absence of the other process steps. Steps d) and f) may be combined in the absence of the other process steps. Steps d), e) and f) may be combined in the absence of the other process steps.

Step a) of the present invention may be carried out as follows:
a) reacting ethyl isonipecotate with 1-bromo-2-chloroethane in the presence of an organic base in a solvent, at a temperature between about 20° C. to about 56° C., to form ethyl 1-(2-chloroethyl) piperidine-4-carboxylate (II); and preferably thereafter (i) performing solvent exchange, removing any salts formed from the reaction mixture, preferably by aqueous extraction, and concentrating the resulting solution to isolate the ethyl 1-(2-chloroethyl) piperidine-4-carboxylate (II) present from solution after filtration to remove the dimer; or thereafter (ii) removing any salts formed from the reaction mixture, preferably by aqueous extraction, acidification of the resulting solution with inorganic or organic acids, preferably hydrochloric acid, acetic acid, succinic acid or oxalic acid and isolating the product ethyl 1-(2-chloroethyl)piperidine-4-carboxylate (II) as a salt, preferably by filtration and drying.

The solvent used in step a) may be selected from the group consisting of ketones such as acetone.

The organic base used in step a) may be selected from the group consisting of organic bases such as amines like triethylamine, pyridine, N,N-diisopropylethylamine, 4-(dimethylamino) pyridine, 1,8-diazabicyclo[5.4.0]undec-7-ene. Preferably the organic base is triethylamine. Upon completion of the reaction of step a), solvent exchange may be performed, triethylamine salts can be removed by aqueous extraction, and the resulting solution can be concentrated to isolate the ethyl 1-(2-chloroethyl)piperidine-4-carboxylate (II). By using triethylamine as the organic base, it is possible to obtain ethyl 1-(2-chloroethyl)piperidine-4-carboxylate (II) in yields up to 66% with a residual content of diethyl 1,1'-(ethane-1,2-diyl) bis(piperidine-4-carboxylate) (V) below 14%. In contrast, by performing the innovator's procedure disclosed in WO2005/104745, the formation of by-product diethyl 1,1'-(ethane-1,2-diyl) bis (piperidine-4-carboxylate) (V) reached 22%.

Step a) may be carried out at a temperature between about 20° C. and about 56° C., preferably between about 20° C. and about 30° C., more preferably the reaction is performed at a temperature between about 20° C. and about 25° C. At temperatures higher than 30° C. more significant amounts of the byproduct diethyl 1,1'-(ethane-1,2-diyl)bis(piperidine-4-carboxylate) (V) are obtained yielding ethyl 1-(2-chloroethyl)piperidine-4-carboxylate (II) in lower yield (34%) Step a) may be carried out for a time period of between about 14 h and about 24 h.

After any salts (e.g. triethylamine salts) have been removed by aqueous extraction, the resulting solution can be acidified with inorganic or organic acids, preferably using hydrochloric acid, acetic acid, succinic acid or oxalic acid or solutions thereof, and the product ethyl 1-(2-chloroethyl) piperidine-4-carboxylate (II) can be isolated as a salt, preferably by filtration and drying.

As disclosed above, step a) may comprise exchanging the reaction solvent. The exchange solvent may comprise one or more alkanes, such as n-heptane or a mixture of heptanes.

As also disclosed above, step a) may comprise removing the dimer by filtration. The reaction mixture may be cooled prior to filtration, optionally being cooled down to about −20° C. and maintained at that temperature for about 12 h to about 24 h, optionally for about 16 h.

In combination, step a) may comprise:
i) exchanging the reaction solvent;
ii) aqueous extraction; and
iii) removing the dimer by filtration.

Step b) of the present invention may be carried out as follows:

b) reacting ethyl 1-(2-chloroethyl)piperidine-4-carboxylate (II) or a salt thereof with lithium diisopropylamide in a solvent, preferably at a temperature between about −50° C. and about 25° C. to form ethyl 1-azabicyclo[2.2.2]octane-4-carboxylate (III) or a salt thereof; and preferably thereafter removing any salts formed from the reaction mixture, preferably by basic aqueous extraction, and performing solvent distillation and solvent exchange.

The solvent used in step b) may be selected from the group consisting of cyclic ethers such as tetrahydrofuran (THF).

Step c) of the present invention may be carried out as follows:

c) reacting ethyl 1-azabicyclo[2.2.2]octane-4-carboxylate (III) or a salt thereof with phenyl lithium in a solvent, preferably at a temperature between about −30° C. to about 25° C. to form 1-azabicyclo[2.2.2]oct-4-yl(diphenyl)methanol (IV) or a salt thereof; preferably treating the reaction mixture containing 1-azabicyclo[2.2.2]oct-4-yl (diphenyl)methanol (IV) or a salt thereof with water and concentrating the resulting solution, and preferably thereafter adding a suitable anti-solvent to effect precipitation, and isolating the product so formed, preferably by filtration and drying, with a purity of ≥98.0% by HPLC.

The solvent used in step c) may be selected from the group consisting of cyclic ethers such as THF.

Step d) of the present invention may be carried out as follows:

d) reacting 1-azabicyclo[2.2.2]oct-4-yl(diphenyl)methanol (IV) with ((2-bromoethoxy) methyl) benzene in a solvent, at a temperature between about 40° C. and about solvent reflux temperature, preferably at a temperature between about 60° C. about solvent reflux temperature to form 4-[hydroxyl(diphenyl)methyl]-1-[2-(phenylmethyl) oxy] ethyl]-1-azoniabicyclo[2.2.2]octane bromide (I), umeclidinium bromide, and preferably cooling down the reaction mixture to a temperature between about −10° C. and about 5° C., preferably stirring the suspension at a temperature between about −10° C. and about 5° C. for about 2 h. Thereafter, the resulting product can be isolated, preferably by filtration and dried at a temperature of between about 35° C. and about 55° C., preferably under vacuum, with a purity of ≥98.0% by HPLC, in a single crystalline form.

The solvent used in step d) may be selected from the group consisting of cyclic ethers such as THF, aromatic solvents, such as toluene, ketones such as acetone, and protic solvents such as water. Step d) may be carried out at a temperature between about 40° C. and about 111° C., preferably optionally between about 60° C. and about 100° C. Preferably the reaction is carried out in water at a temperature between about 60° C. to about 100° C. Step d) may be carried out for a time period of between about 18 h to about 24 h. When the reaction is complete, cooling down the reaction allows umeclidinium bromide to be obtained in yields up to 84%. The purity of the product obtained by following the procedure described is typically ≥98.0% by HPLC, in a single crystalline form. The crystalline form of the isolated umeclidinium bromide is an unsolvated form of umeclidinium bromide.

Step e) of the present invention may be carried out as follows:

e) recrystallizing the umeclidinium bromide in a solvent, at a temperature between about 40° C. to about solvent reflux temperature, preferably at a temperature between about 60° C. to about 80° C. to obtain 4-[hydroxyl (diphenyl)methyl]-1-[2-(phenylmethyl)oxy]ethyl]-1-azoniabicyclo [2.2.2]octane bromide (I), umeclidinium bromide, and preferably cooling down the reaction mixture to a temperature between about −10° C. and about 5° C., preferably stirring the suspension at a temperature between about −10° C. and about 5° C. for about 2 h. Thereafter, the resulting product is isolated, preferably by filtration and dried at a temperature of between about 35° C. and about 55° C., preferably under vacuum, to provide a product with a purity of ≥99.0% by HPLC and in a single crystalline form.

Umeclidinium bromide obtained according to the step d) of the present invention can be recrystallized. The recrystallization solvents may be selected from the group consisting of alcohols, such as 1-propanol, protic solvents such as water or mixtures of both classes of solvents. Preferably recrystallization is carried out in water, optionally by suspending the material in water at a temperature between about 40° C. to about solvent reflux temperature, preferably at a temperature between about 60° C. and about 80° C. The resulting solution may be cooled to a temperature between about −10° C. and about 5° C. and the resulting suspension may be stirred at a temperature between about −10° C. and about 5° C. for about 2 hours. Preferably, umeclidinium bromide is isolated (optionally by filtration), washed with water (optional) and then dried. The umeclidinium bromide may be dried under vacuum at a temperature between about 35° C. and about 55° C. The dried product typically has a purity ≥99.0% by HPLC and exhibits a single crystalline form.

The X-Ray Powder Diffraction (XRPD) diffractogram, the Differential Scanning calorimetry (DSC) thermogram, the Thermogravimetric Analysis (TGA) thermogram and HPLC chromatogram of a product obtained according to the present invention are presented in FIGS. 1-9.

Umeclidinium bromide obtained from the present invention is preferably micronized to obtain material with a particle size suitable for inhalation. Therefore, the present invention also provides a micronization process for tailoring the particle size whilst maintaining the crystalline form of umeclidinium bromide.

EXAMPLES

The following examples are provided to illustrate the process of the present invention and are not intended to be construed as limitations of the present invention; minor variations may be resorted to without departing from the spirit and scope of the present invention.

Example 1

Preparation of ethyl 1-(2-chloroethyl)-4-piperidine-4-carboxylate (II)

Triethylamine (1.09 mL, 7.79 mmol) was added to a solution of ethyl isonipecotate (0.80 mL, 5.19 mmol) in acetone (7.20 mL) followed by 1-bromo-2-chloroethane (0.86 mL, 10.38 mmol). The reaction mixture was stirred for 24 h at 25° C. and then concentrated under vacuum. The resulting residue was treated with water (3.0 mL) and extracted with ethyl acetate (3×3.0 mL). The combined organic layers were dried with MgSO$_4$, filtered and concentrated under vacuum. The purification of the crude product was performed by flash chromatography on silica gel (gradient 1:1 n-hexane/ethyl acetate to 9:1 ethyl acetate/methanol) resulting in the desired compound (colorless liquid, 0.75 g, 65.6%) and the respective dimer (0.25 g, 14.0%).

Ethyl 1-(2-chloroethyl)-4-piperidine-4-carboxylate (II): $^1$H-NMR (300 MHz, CDCl$_3$) δ 4.11 (q, J=5.3 Hz, 2H), 3.55 (t, J=4.0 Hz, 2H), 2.88-2.84 (m, 2H), 2.68 (t, J=4.0 Hz, 2H), 2.24 (dt, J=12.0, 3.0 Hz, 1H), 2.12 (td, J=11.3, 2.7 Hz, 2H), 1.93-1.65 (m, 4H), 1.22 (t, J=9.0 Hz, 3H); $^{13}$C-NMR (75 MHz, CDCl$_3$) δ 175.11, 60.51, 60.21, 53.18, 41.23, 41.09, 28.29, 14.38. MS (ESI) m/z calculated for C$_{10}$H$_{18}$ClNO$_2$: 219, found 220 [M+H]$^+$.

Diethyl 1,1'-(ethane-1,2-diyl)bis(piperidine-4-carboxylate) (V): $^1$H-NMR (300 MHz, CDCl$_3$) δ 4.11 (q, J=5.25 Hz, 4H), 2.99-2.76 (m, 4H), 2.47 (s, 4H), 2.30-2.20 (m, 2H), 2.07-1.99 (m, 6H), 1.90-1.84 (m, 4H), 1.79-1.66 (m, 4H), 1.23 (t, J=6.0 Hz, 6H); $^{13}$C-NMR (75 MHz, CDCl$_3$) δ 175.29, 60.49, 56.43, 53.68, 41.29, 28.40, 14.40. MS (ESI) m/z calcd for C$_{18}$H$_{32}$N$_2$O$_2$: 340, found 341 [M+H]$^+$.

Example 2

Preparation of ethyl 1-(2-chloroethyl)-4-piperidine-4-carboxylate (II)

Triethylamine (1.09 mL, 7.79 mmol) was added to a solution of ethyl isonipecotate (0.80 mL, 5.19 mmol) in acetone (8.60 mL) followed by 1-bromo-2-chloroethane (0.86 mL, 10.38 mmol). The reaction mixture was stirred for 17 h at 25° C. n-heptane (8.6 mL) was then added and the acetone was removed under vacuum. To the resultant mixture, n-heptane (8.6 mL) was added again and more acetone was removed under vacuum to obtain a volume of 8.6 mL. Water (8.6 mL) was added to the mixture and extracted with n-heptane (2×8.6 mL). The combined organic layers were dried with MgSO$_4$, filtered and concentrated under vacuum. Further n-heptane was added (2.40 mL) and the solution was placed at 0° C. for 1 h and cooled down to –20° C. for 16 h. The solution was filtered to remove dimer (diethyl 1,1'-(ethane-1,2-diyl)bis(piperidine-4-carboxylate) (V)) and then concentrated under vacuum. The purification of the crude product was performed by flash chromatography on silica gel (gradient 1:1 n-hexane/ethyl acetate to 9:1 ethyl acetate/methanol) resulting in the desired compound (colorless liquid, 0.63 g, 55.1%) and the respective dimer (0.10 g, 5.8%).

Example 3

Preparation of ethyl 1-(2-chloroethyl)-4-piperidine-4-carboxylate (II)

A solution of ethyl isonipecotate (0.40 mL, 2.60 mmol) and triethylamine (0.55 mL, 3.90 mmol) in acetone (1.3 mL) was slowly added over 5 h to a solution of 1-bromo-2-chloroethane (0.43 mL, 5.19 mmol) in acetone (3.0 mL) at 56° C. The reaction mixture was stirred for 24 h at 56° C. and then concentrated under vacuum. The resulting residue was treated with water (1.0 mL) and extracted with diethyl ether (3×3.0 mL). The combined organic layers were dried with MgSO$_4$, filtered and concentrated under vacuum. The purification of the crude product was performed by flash chromatography on silica gel 6:4 n-hexane/ethyl acetate) resulting in the desired compound (colorless liquid, 0.19 g, 33.5%) and the respective dimer.

Example 4

Preparation of ethyl 1-(2-chloroethyl)-4-piperidine-4-carboxylate (II)

A solution of ethyl isonipecotate (0.40 mL, 2.60 mmol) and triethylamine (0.55 mL, 3.90 mmol) in acetone (1.6 mL) was slowly added over 5 h to a solution of 1-bromo-2-chloroethane (0.86 mL, 10.38 mmol) and potassium iodide (10%, 1.04 mmol, 0.17 mg) in acetone (7.0 mL) at room temperature. The reaction mixture was stirred for 24 h at 25° C. and then concentrated under vacuum. The resulting residue was treated with water (1.0 mL) and extracted with diethyl ether (3×3.0 mL). The combined organic layers were dried with MgSO$_4$, filtered and concentrated under vacuum. The purification of the crude product was performed by flash chromatography on silica gel (6:4 n-hexane/ethyl acetate) resulting in the desired compound (colorless liquid, 0.29 g, 50.1%) and the respective dimer.

Example 5

Preparation of ethyl 1-(2-chloroethyl)-4-piperidine-4-carboxylate (II)

N,N-diisopropylethylamine (DIPEA) (1.36 mL, 7.79 mmol) was added to a solution of ethyl isonipecotate (0.80 mL, 5.19 mmol) in acetone (8.60 mL) followed by 1-bromo-2-chloroethane (0.86 mL, 10.38 mmol). The reaction mixture was stirred for 24 h at 25° C. Water (3.0 mL) was then added, the pH was neutralized with HCl (1M) and the aqueous phase was extracted with diethyl ether (3×10.0 mL). The combined organic layers were dried with MgSO$_4$, filtered and concentrated under vacuum. The crude product (0.67 g) was analyzed by $^1$H-NMR resulting in a 1.00:0.06 ethyl 1-(2-chloroethyl)-4-piperidine-4-carboxylate (II) to dimer.

Example 6

Preparation of ethyl 1-(2-chloroethyl)-4-piperidine-4-carboxylate (II)

4-dimethylaminopyridine (DMAP) (0.95 g, 7.79 mmol) was added to a solution of ethyl isonipecotate (0.80 mL, 5.19 mmol) in acetone (8.60 mL) followed by 1-bromo-2-chloroethane (0.86 mL, 10.38 mmol). The reaction mixture was stirred for 24 h at 25° C. Water (3.0 mL) was then added, the pH was neutralized with HCl (1M) and the aqueous phase was extracted with diethyl ether (3×10.0 mL). The combined organic layers were dried with MgSO$_4$, filtered and concentrated under vacuum. The crude product (0.52 g) was analyzed by $^1$H-NMR resulting in a 1.00:0.06 ethyl 1-(2-chloroethyl)-4-piperidine-4-carboxylate (II) to dimer.

Example 7

Preparation of ethyl 1-(2-chloroethyl)-4-piperidine-4-carboxylate (II)

1,8-diazabicycloundec-7-ene (DBU) (1.16 mL, 7.79 mmol) was added to a solution of ethyl isonipecotate (0.80 mL, 5.19 mmol) in acetone (8.60 mL) followed by 1-bromo-2-chloroethane (0.86 mL, 10.38 mmol). The reaction mixture was stirred for 24 h at 25° C. Water (3.0 mL) was then added, the pH was neutralized with HCl (1M) and the aqueous phase was extracted with diethyl ether (3×10.0 mL). The combined organic layers were dried with MgSO$_4$, filtered and concentrated under vacuum. The crude product (0.88 g) was analyzed by $^1$H-NMR and the dimer was not detected.

Example 8

Preparation of ethyl 1-(2-chloroethyl)-4-piperidine-4-carboxylate (II)

Pyridine (0.63 mL, 7.79 mmol) was added to a solution of ethyl isonipecotate (0.80 mL, 5.19 mmol) in acetone (8.60 mL) followed by 1-bromo-2-chloroethane (0.86 mL, 10.38 mmol). The reaction mixture was stirred for 24 h at 25° C. n-heptane (8.6 mL) was then added and the acetone was removed under vacuum. To the resultant mixture, n-heptane (8.6 mL) was added again and more acetone was removed under vacuum to obtain a volume of 8.6 mL. Water (8.6 mL) was added to the mixture and extracted with n-heptane (2×8.6 mL). The combined organic layers were dried with MgSO$_4$, filtered and concentrated under vacuum. The crude product (0.38 g) was analyzed by 1H-NMR resulting in 1.00:0.10 ratio of ethyl 1-(2-chloroethyl)-4-piperidine-4-carboxylate (II) to dimer.

Example 9

Preparation of ethyl 1-(2-chloroethyl)-4-piperidine-4-carboxylate hydrochloride

To a solution of ethyl 1-(2-chloroethyl)-4-piperidine-4-carboxylate (II) (0.15 mL) in ethyl acetate (2 mL) was added hydrogen chloride (1.25 M) in ethanol (0.72 mL), drop by drop, at room temperature. The solvent was removed under vacuum, resulting in a crystalline white solid.

Example 10

Preparation of ethyl 1-azabicyclo[2.2.2]octane-4-carboxylate (III)

A solution of ethyl 1-(2-chloroethyl)-4-piperidine-4-carboxylate (II) (5.0 g, 22.76 mmol) in tetrahydrofuran (THF, 147.0 mL) was cooled down to −50° C. under nitrogen. LDA (2.0 M in heptane/THF/ethyl benzene, 17.0 mL, 34.0 mmol) was added to the solution at −50° C. over 25 mins. The reaction mixture was allowed to warm up to room temperature over 16 h. The reaction was quenched with saturated aqueous K$_2$CO$_3$ (122.0 mL) and extracted with diethyl ether (3×120.0 mL). The combined organic layers were dried with Mg$_S$O$_4$, filtered and concentrated under vacuum. The resulting orange liquid was co-evaporated three times with dichloromethane to remove excess ethyl benzene, resulting in an orange oil (4.15 g, 99.4%). Ethyl 1-azabicyclo[2.2.2]octane-4-carboxylate (III): $^1$H-NMR (300 MHz, CDCl$_3$) δ 4.10 (t, J=5.23 Hz, 2H), 2.90-2.85 (m, 6H), 1.71-1.66 (m, 6H), 1.22 (t, J=4.0 Hz, 3H).

Example 11

Preparation of 1-azabicyclo[2.2.2]oct-4-yl(diphenyl)methanol (IV)

A solution of phenyllithium (1.9 M in 70 cyclohexane/30 ether, 22.30 mL, 42.40 mmol) was cooled down to −30° C. under nitrogen. A solution of ethyl 1-azabicyclo[2.2.2]octane-4-carboxylate (III, 2.0 g, 10.90 mmol) in THF (27.0 mL) was slowly added to the reaction mixture at −30° C. over 25 mins. The reaction mixture was allowed to warm up to room temperature over 16 h. The reaction was quenched with water (10.0 mL) and then evaporated to dryness under vacuum. Water (40.0 mL) and ethyl acetate (40.0 mL) were added, causing a white solid to crash out. This solid was filtered off under vacuum, to give a white powder (2.46 g, 76.8%). 1-azabicyclo[2.2.2]oct-4-yl(diphenyl)methanol (IV): $^1$H-NMR (300 MHz, CDCl$_3$) δ 7.54-7.51 (m, 3H), 7.33-7.20 (m, 6H), 2.85-2.80 (m, 6H), 1.78-1.72 (m, 6H). MS (ESI) m/z calcd for C$_{20}$H$_{23}$NO: 293, found 294 [M+H]+.

Example 12

Preparation of 4-[hydroxyl(diphenyl)methyl]-1-[2 (phenylmethyl)oxy]ethyl}-1-azoniabicyclo [2.2.2] octane bromide (I)

To a solution of 1-azabicyclo[2.2.2]oct-4-yl(diphenyl) methanol (IV, 0.20 g, 0.69 mmol) in THF (30.0 mL) was added ((2-bromoethoxy)methyl)benzene (0.16 mL, 1.03 mmol). The solution was stirred for 24 h at 60° C. Then the solution was cooled down to 25° C. and concentrated under vacuum, forming a white solid. The product was filtered and washed with ethyl acetate (5×20.0 mL) and n-hexane (5×20.0 mL) under vacuum. The white solid was then dried under vacuum (0.30 g, 82.2%).

4-[hydroxyl(diphenyl)methyl]-1-[2(phenylmethyl)oxy] ethyl}-1-azoniabicyclo[2.2.2]octane bromide (I): $^1$H-NMR (300 MHz, DMSO-d$_6$) δ 7.54 (d, J=6.0 Hz, 4H), 7.35-7.20 (m, 11H), 5.97 (s, 1H), 4.49 (s, 2H), 3.81 (b, 2H), 3.49-3.46 (m, 6H), 3.31 (s, 2H), 1.99 (bt, J=6.0 Hz, 6H). MS (ESI) m/z calcd for C$_{29}$H$_{34}$NO$_2$: 428, found 428 [M H]$^+$.

Example 13

Preparation of 4-[hydroxyl(diphenyl)methyl]-1-[2 (phenylmethyl)oxy]ethyl}-1-azoniabicyclo [2.2.2] octane bromide (I)

To a suspension of 1-azabicyclo[2.2.2]oct-4-yl(diphenyl) methanol (IV, 0.20 g, 0.69 mmol) in acetone (30.0 mL) was added ((2-bromoethoxy)methyl)benzene (0.16 mL, 1.03 mmol). The reaction mixture was stirred for 24 h at 60° C. Then the reaction mixture was cooled down to 25° C. and concentrated under vacuum, forming a white solid. The product was filtered and washed with ethyl acetate (5×20.0 mL) and n-hexane (5×20.0 mL) under vacuum. The white solid was then dried under vacuum (0.27 g, 75.7%).

Example 14

Preparation of 4-[hydroxyl(diphenyl)methyl]-1-[2 (phenylmethyl)oxy]ethyl}-1-azoniabicyclo [2.2.2] octane bromide (I)

To a suspension of 1-azabicyclo[2.2.2]oct-4-yl(diphenyl) methanol (IV, 0.20 g, 0.69 mmol) in toluene (30.0 mL) was added ((2-bromoethoxy)methyl)benzene (0.16 mL, 1.03 mmol). The reaction mixture was stirred for 24 h at 60° C. Then the solution was cooled down to 25° C. and concentrated under vacuum, forming a white solid. The product was filtered and washed with ethyl acetate (5×20.0 mL) and n-hexane (5×20.0 mL) under vacuum. The white solid was then dried under vacuum (0.28 g, 79.6%).

Example 15

Preparation of 4-[hydroxyl(diphenyl)methyl]-1-[2 (phenylmethyl)oxy]ethyl}-1-azoniabicyclo [2.2.2] octane bromide (I)

To a suspension of 1-azabicyclo[2.2.2]oct-4-yl(diphenyl) methanol (IV, 0.20 g, 0.69 mmol) in toluene (30.0 mL) was added ((2-bromoethoxy)methyl)benzene (0.16 mL, 1.03 mmol). The reaction mixture was stirred for 24 h under reflux. Then the reaction mixture was slowly cooled down to a temperature between 2° C. and 4° C. wherein a white solid precipitated. The product was filtered and washed with ethyl acetate (5×20.0 mL) and n-hexane (5×20.0 mL) under vacuum. The white solid was then dried under vacuum (0.28 g, 79.6%).

Example 16

Preparation of 4-[hydroxyl(diphenyl)methyl]-1-[2 (phenylmethyl)oxy]ethyl}-1-azoniabicyclo [2.2.2] octane bromide (I)

To a suspension of 1-azabicyclo[2.2.2]oct-4-yl(diphenyl) methanol (IV, 0.20 g, 0.69 mmol) in water (20.0 mL) was added ((2-bromoethoxy)methyl)benzene (0.16 mL, 1.03 mmol). The reaction mixture was stirred for 24 h under reflux. Then the reaction mixture was slowly cooled down to a temperature between 2° C. and 4° C. wherein a white solid precipitated. The product was filtered and washed with ethyl acetate (20.0 mL) and n-hexane (5×20.0 mL) under vacuum. The white solid was then dried under vacuum (0.24 g, 68.3%).

Example 17

Preparation of 4-[hydroxyl(diphenyl)methyl]-1-[2 (phenylmethyl)oxy]ethyl}-1-azoniabicyclo [2.2.2] octane bromide (I)

To a suspension of 1-azabicyclo[2.2.2]oct-4-yl(diphenyl) methanol (IV, 0.20 g, 0.69 mmol) in water (15.0 mL) and acetone (15.0 mL) was added ((2-bromoethoxy)methyl) benzene (0.16 mL, 1.03 mmol). The reaction mixture was stirred for 24 h at 60° C. Then the reaction mixture was slowly cooled down to a temperature between 2° C. and 4° C. wherein a white solid precipitated. The product was filtered and washed with ethyl acetate (20.0 mL) and n-hexane (5×20.0 mL) under vacuum. The white solid was then dried under vacuum (0.19 g, 54.2%).

Example 18

Preparation of 4-[hydroxyl(diphenyl)methyl]-1-[2 (phenylmethyl)oxy]ethyl}-1-azoniabicyclo [2.2.2] octane bromide (I)

To a suspension of 1-azabicyclo[2.2.2]oct-4-yl(diphenyl) methanol (IV, 0.75 g, 2.56 mmol) in water (112.50 mL) was added ((2-bromoethoxy)methyl)benzene (0.61 mL, 3.83 mmol). The reaction mixture was stirred for 24 h at 60° C. Then the reaction mixture was slowly cooled down to a temperature between 2° C. and 4° C. and stirred for 2 h at a temperature between 2° C. and 4° C. The product was filtered and washed with ethyl acetate (20.0 mL) and n-hexane (5×20.0 mL) under vacuum. The white solid was then dried under vacuum (1.03 g, 78.9%).

Example 19

Preparation of 4-[hydroxyl(diphenyl)methyl]-1-[2 (phenylmethyl)oxy]ethyl}-1-azoniabicyclo [2.2.2] octane bromide (I)

Triethylamine (5.45 mL, 38.95 mmol) was added to a solution of ethyl isonipecotate (4.0 mL, 25.95 mmol) in acetone (43.0 mL) followed by 1-bromo-2-chloroethane (4.32 mL, 52.14 mmol). The reaction mixture was stirred for 17 h at 25° C. n-heptane (43.0 mL) was then added and the acetone was removed under vacuum. To the resultant mixture, n-heptane (43.0 mL) was added again and more acetone was removed under vacuum to obtain a volume of 43.0 mL. Water (43.0 mL) was added to the mixture and extracted with n-heptane (2×43.0 mL). The combined organic layers were dried with $MgSO_4$, filtered and concentrated under vacuum. This first crude product (4.02 g) was analyzed by $^1$H-NMR resulting in 1.00:0.11 ratio of ethyl 1-(2-chloroethyl)-4-piperidine-4-carboxylate (II) to dimer. Further n-heptane (11.50 mL) was added to the crude product and the solution was placed at 0° C. for 1 h and cooled down to −20° C. for 16 h. The solid was filtered to remove dimer and then the solution of ethyl 1-(2-chloroethyl)-4-piperidine-4-carboxylate (II) was concentrated under vacuum. This second crude product (3.57 g) was analyzed by $^1$H-NMR resulting in a 1.00:0.09 ratio of ethyl 1-(2-chloroethyl)-4-piperidine-4-carboxylate (II) to dimer.

A solution of the second crude product (ethyl 1-(2-chloroethyl)-4-piperidine-4-carboxylate (II) 3.57 g) in THF (89.6 mL) was cooled down to −50° C. under nitrogen. LDA (1.0 M in hexanes/THF 20.72 mL, 20.72 mmol) was added to the solution at −50° C. over 25 mins. The reaction mixture was allowed to warm up to room temperature over 16 h. The reaction was quenched with saturated aqueous solution of $K_2CO_3$ (74.4 mL) and extracted with ethyl acetate (3×74.4 mL). The combined organic layers were dried with $MgSO_4$, filtered and concentrated under vacuum, to give crude ethyl 1-azabicyclo[2.2.2]octane-4-carboxylate (III) as an orange oil (3.02 g).

A solution of phenyllithium (1.9M in 70 cyclohexane/30 ether, 33.7 mL, 64.1 mmol) was cooled down to −30° C., under nitrogen. A solution of the crude ethyl 1-azabicyclo [2.2.2]octane-4-carboxylate (III, 3.02 g) in THF (36.7 mL) was slowly added to the reaction mixture at −30° C. over 25 mins. The reaction mixture was allowed to warm up to room temperature over 16 h. The reaction was quenched with water (15 mL) and then evaporated to dryness under vacuum (result: yellow solid). Water (60.2 mL) and ethyl acetate (60.2 mL) were added, causing a white solid to crash out. This solid was filtered off under vacuum, to give crude 1-azabicyclo[2.2.2]oct-4-yl (diphenyl)methanol (IV) as a white powder (1.76 g, three steps yield: 23.0%)

To a suspension of the crude 1-azabicyclo[2.2.2]oct-4-yl (diphenyl)methanol (IV, 1.76 g, 5.83 mmol) in water (258.0 mL) was added ((2-bromoethoxy)methyl)benzene (1.40 mL, 9.01 mmol). The reaction mixture was stirred for 24 h under reflux. Then the reaction mixture was slowly cooled down to a temperature between 2° C. and 4° C. and stirred for 2 h at a temperature between 2° C. and 4° C. The product was filtered under vacuum and excess bromide was removed by washing the compound with heptane (20.0 mL). The white solid was then dried under vacuum (2.55 g, final step yield 84.0%).

Example 20

Recrystallization of 4-[hydroxyl(diphenyl)methyl]-1-[2 (phenylmethyl)oxy]ethyl}-1-azoniabicyclo [2.2.2]octane bromide (I)

A suspension of 4-[hydroxyl(diphenyl)methyl]-1-[2(phenylmethyl)oxy]ethyl}-1-azoniabicyclo [2.2.2]octane bromide (I, 0.20 g) in water (2.25 mL) was heated up 80° C. The solution was stirred for 1 h then slowly cooled down to a temperature between 2° C. and 4° C. and stirred for 2 h at a temperature between 2° C. and 4° C. The solid was filtered and dried under vacuum (0.185 g, 92.5%).

Example 21

Micronization of 4-[hydroxyl(diphenyl)methyl]-1-[2 (phenylmethyl)oxy]ethyl}-1-azoniabicyclo [2.2.2] octane bromide (I)

4-[hydroxyl(diphenyl)methyl]-1-[2(phenylmethyl) oxy] ethyl}-1-azoniabicyclo[2.2.2]octane bromide (I, 3.0 g) was fed to a fluid energy jet mill at 10 g/h, operated with $N_2$ at a pressure of 4 bar for the venturi and a pressure of 3 bar for the ring.

Figure 1:
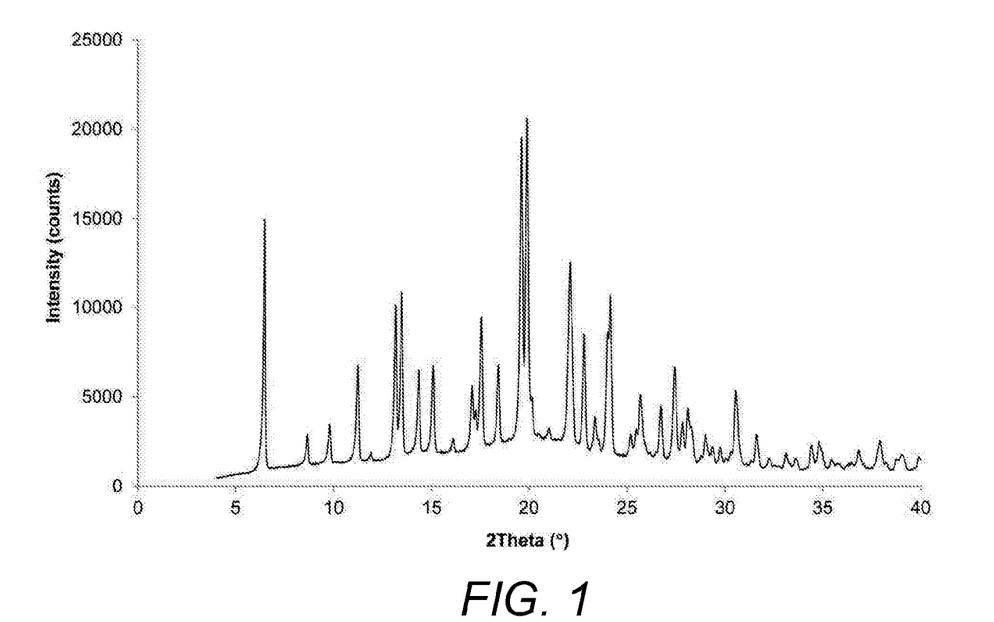
FIG. 1: XRPD diffractogram of umeclidinium bromide obtained from Example 18.
Figure 2:
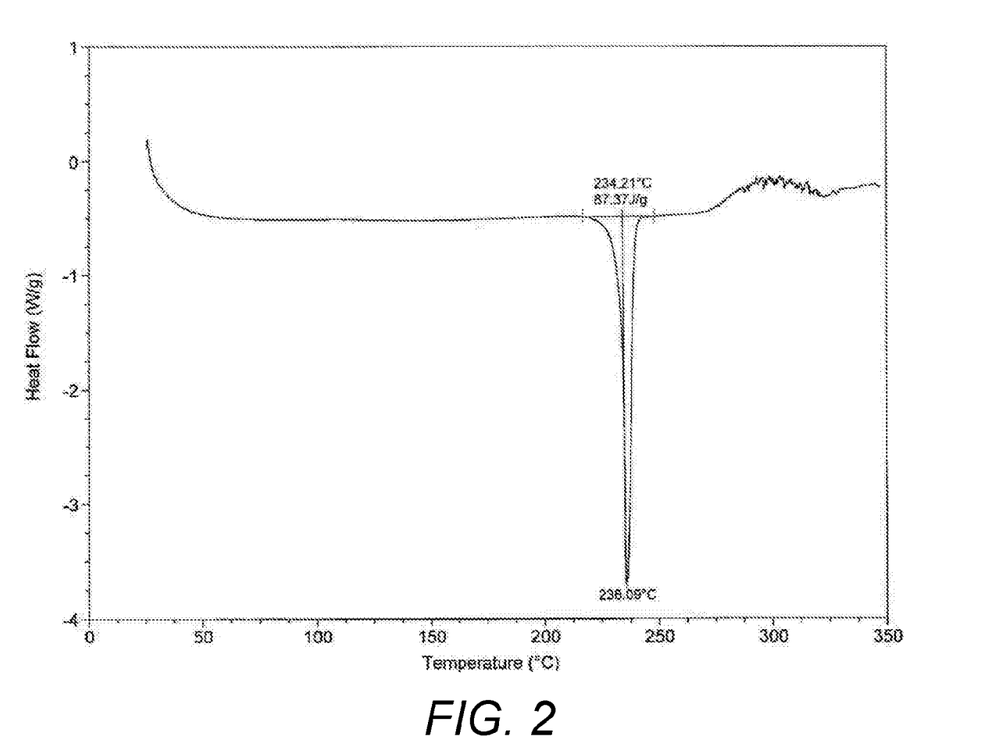
FIG. 2: DSC thermogram of umeclidinium bromide obtained from Example 18.
Figure 3:
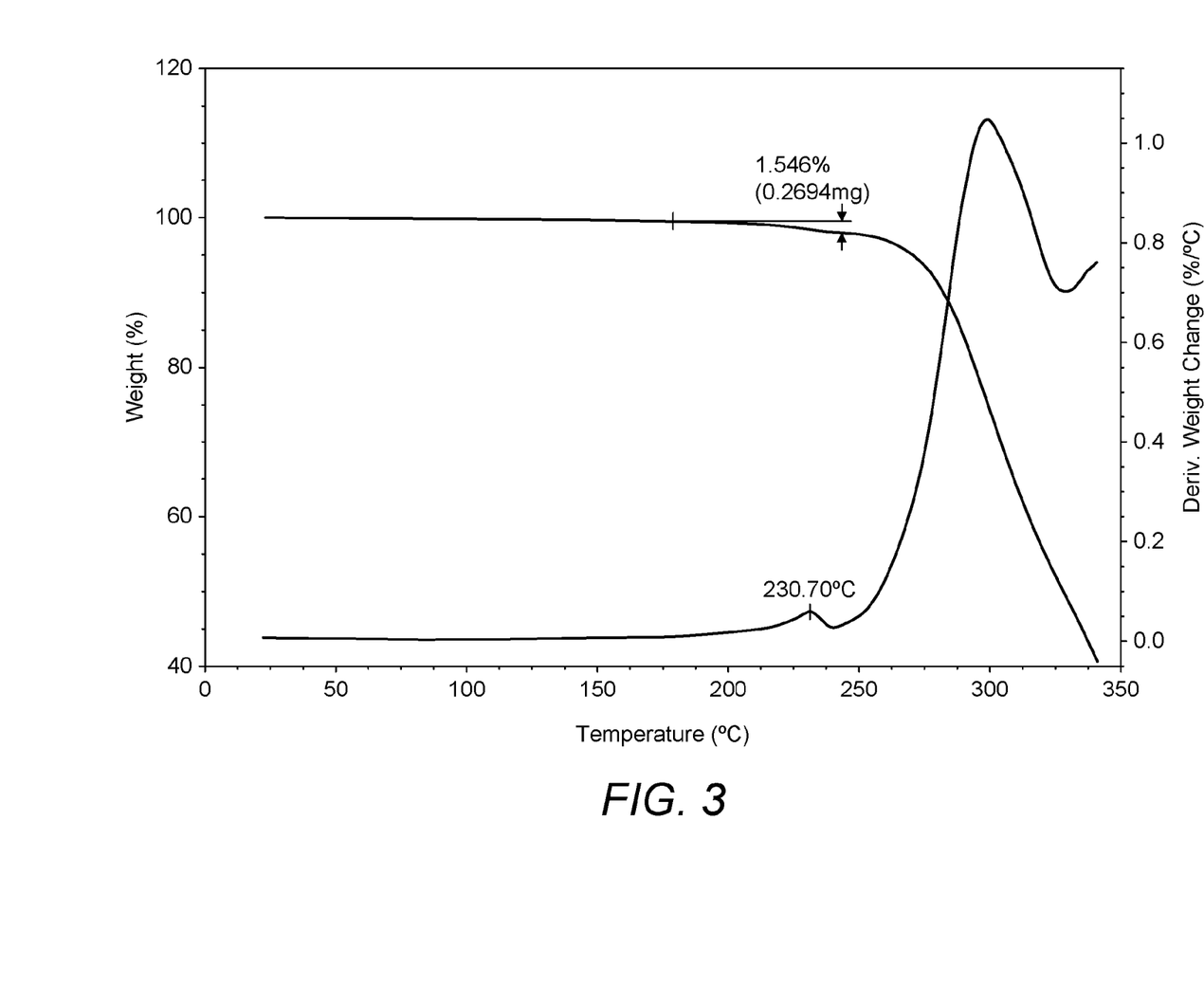
FIG. 3: TGA thermogram of umeclidinium bromide obtained from Example 18.
Figure 4:
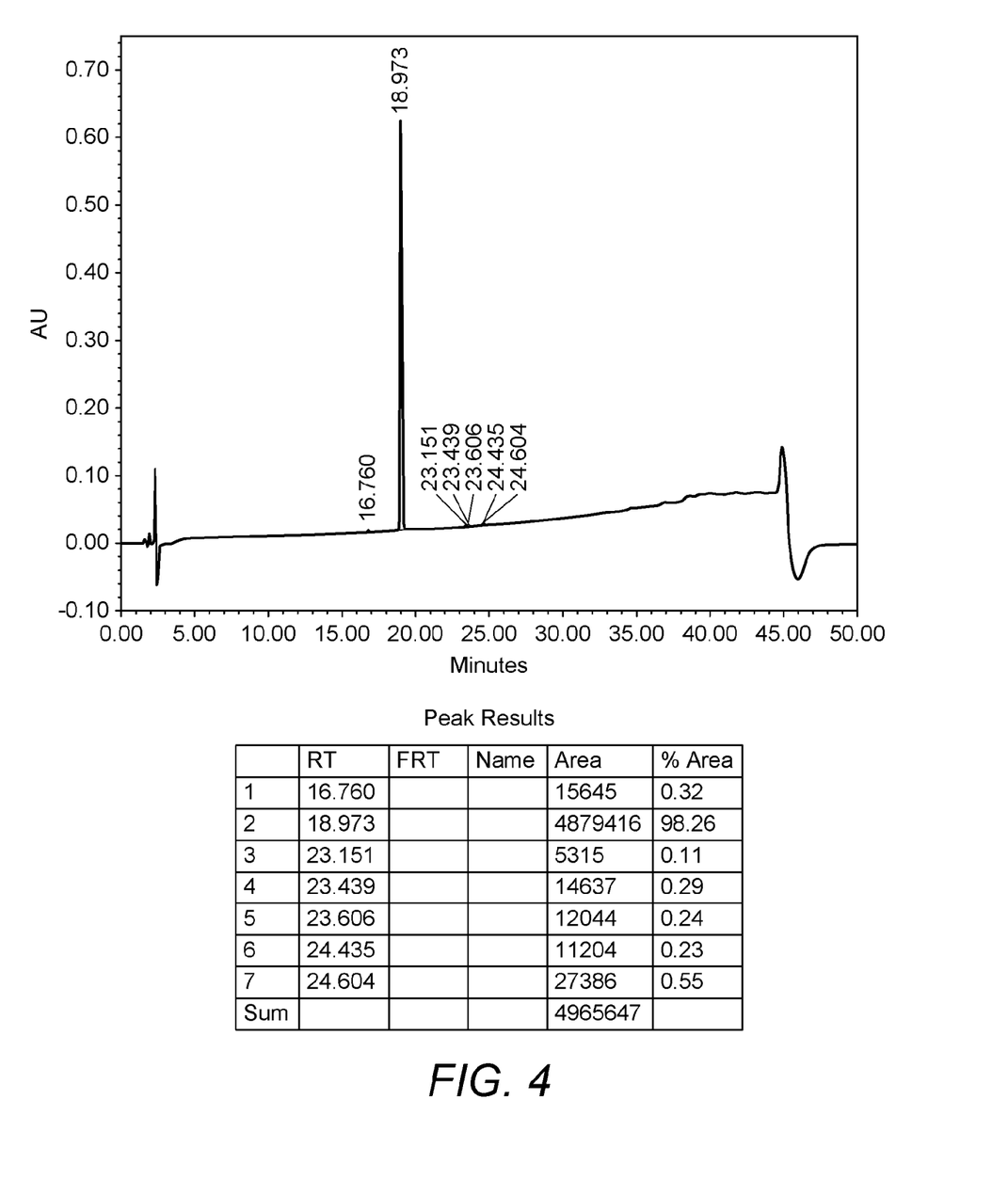
FIG. 4: HPLC of umeclidinium bromide obtained from Example 18.
Figure 5:
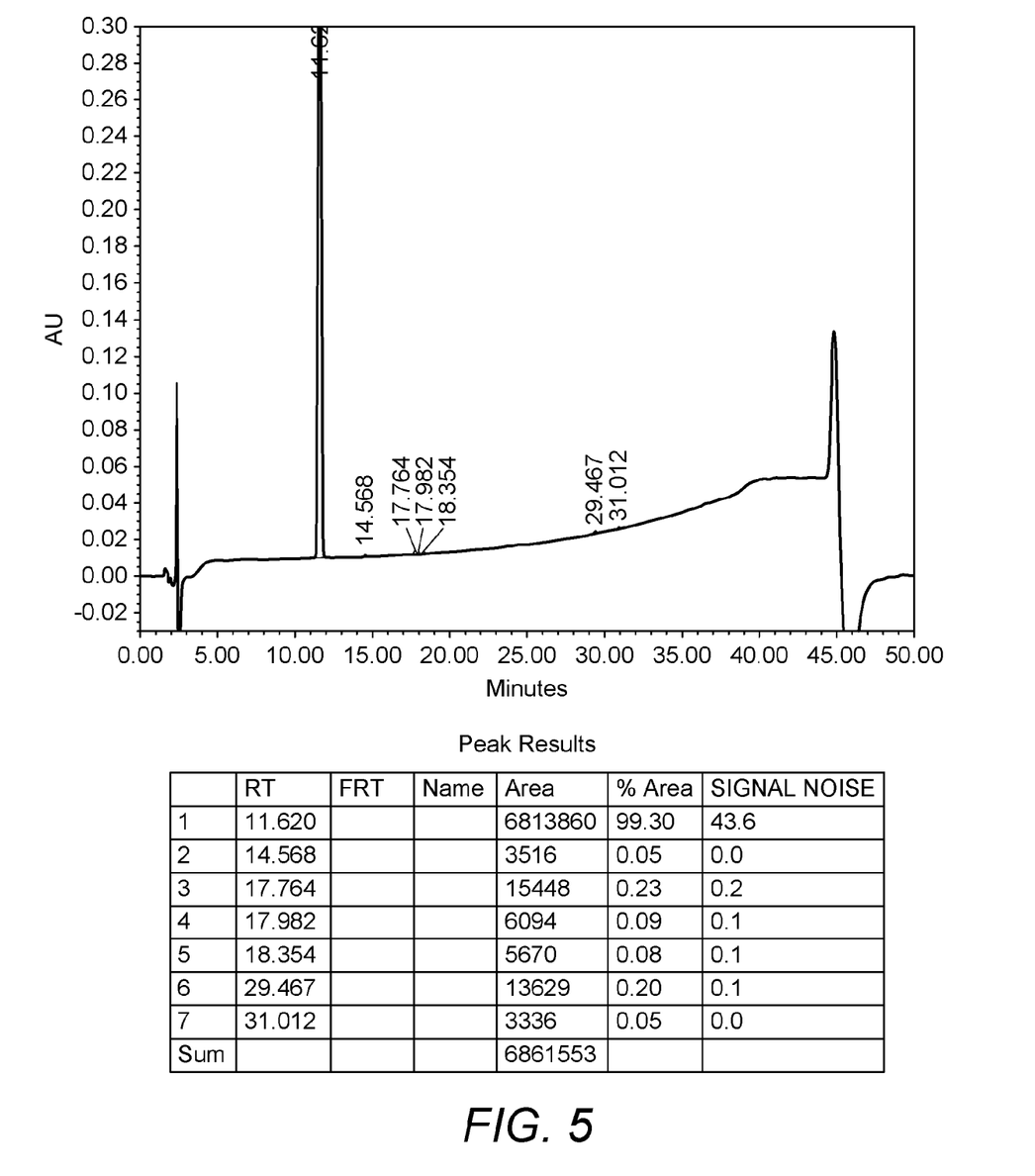
FIG. 5: HPLC of 1-azabicyclo[2.2.2]oct-4-yl(diphenyl) methanol (IV) obtained after three steps of Example 19 and used as the starting material in the final step to prepare umeclidinium bromide.
Figure 6:
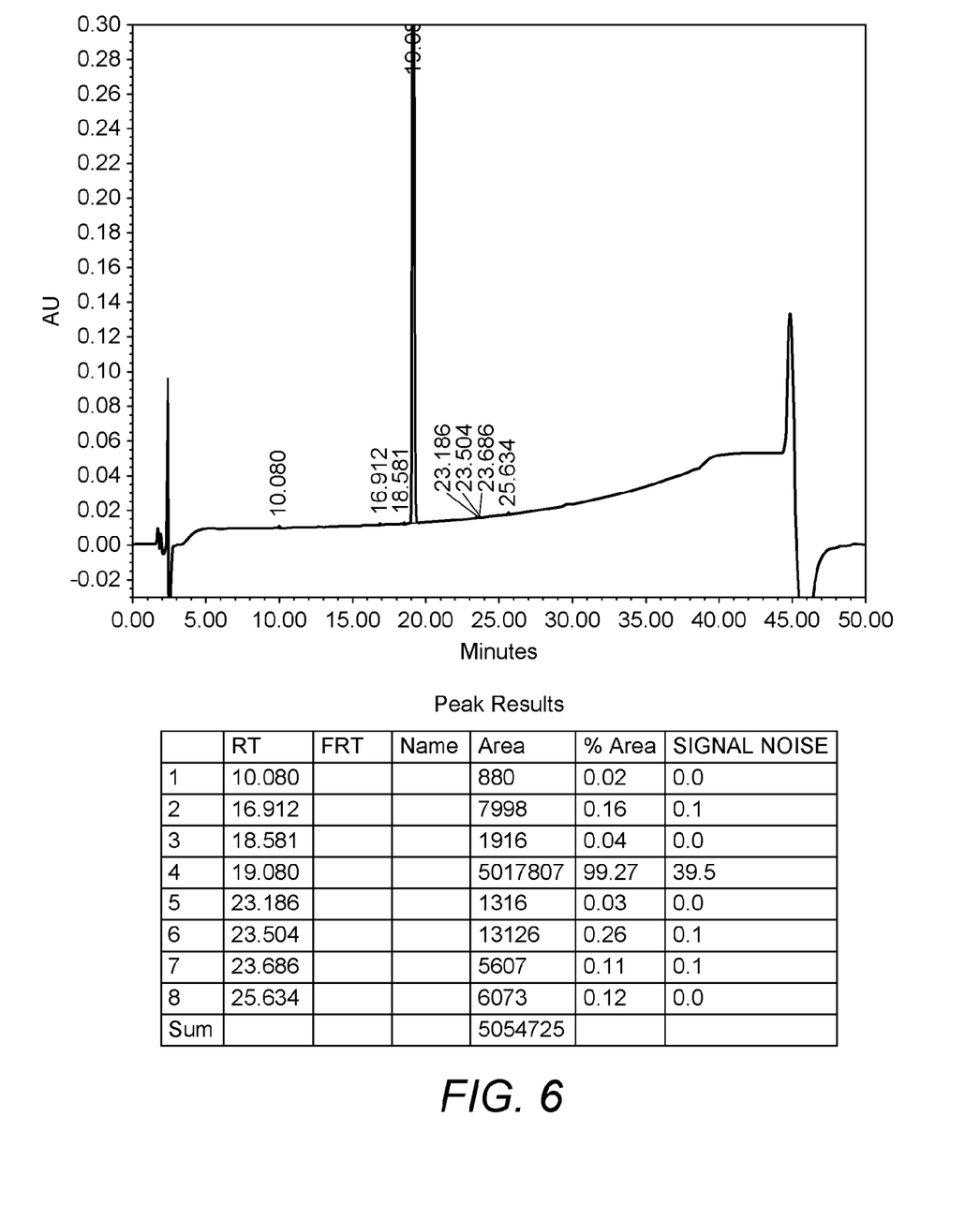
FIG. 6: HPLC umeclidinium bromide recrystallized from water from Example 20.
Figure 7:
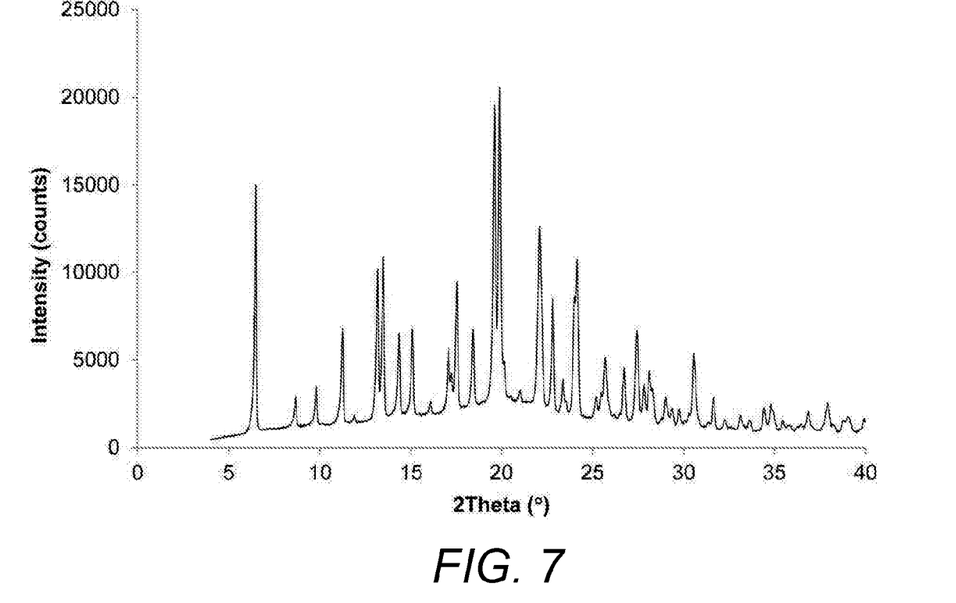
FIG. 7: XRPD umeclidinium bromide before micronization.
Figure 8:
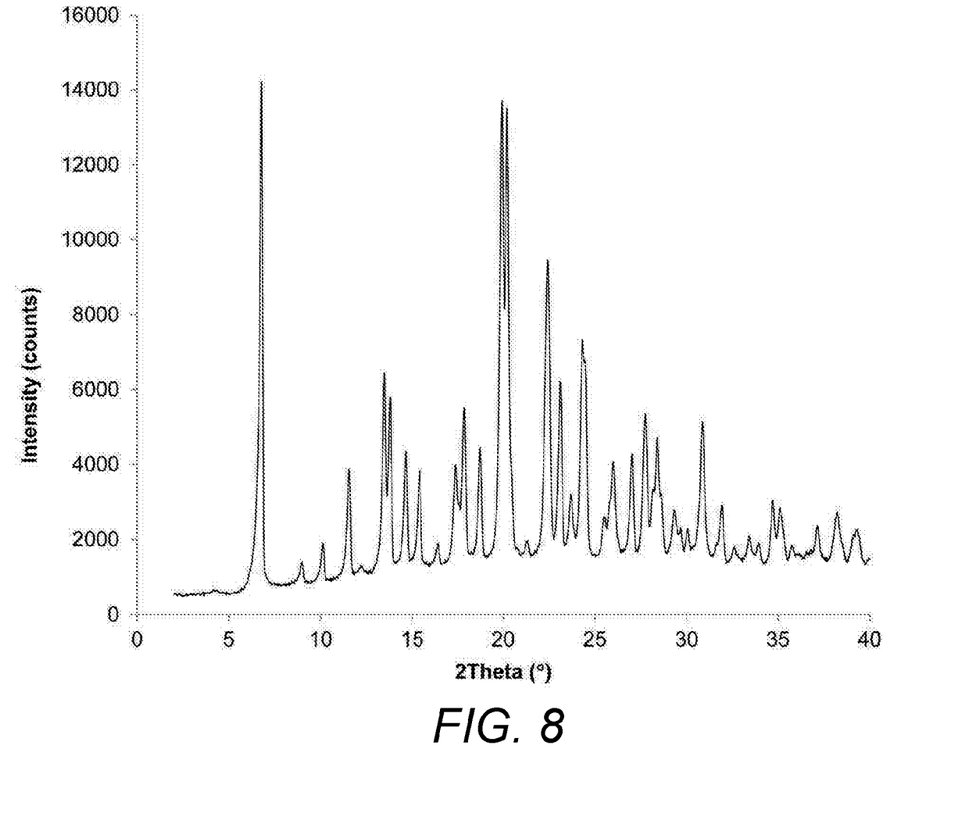
FIG. 8: XRPD umeclidinium bromide after fluid energy jet mill micronization from Example 21.

The isolated product presented an XRPD identical to that of the starting material with a particle size distribution of Dv10=0.664 μm; Dv50=3.071 μm; Dv90=7.013 μm; span=2.07, as depicted in FIG. 8.

Example 22

Micronization of 4-[hydroxyl(diphenyl)methyl]-1-[2 (phenylmethyl)oxy]ethyl}-1-azoniabicyclo [2.2.2] octane bromide (I)

4-[hydroxyl(diphenyl)methyl]-1-[2(phenylmethyl) oxy] ethyl}-1-azoniabicyclo[2.2.2]octane bromide (I, 15.0 g) was suspended in water (285.0 g) and stirred until a uniform suspension was obtained. The uniform suspension was fed to a lab scale High Pressure Homogenization equipment operated at a pressure of 60 bar for 100 cycles in total. After the homogenisation step the suspension was transferred to a holding vessel. The homogenised suspension was fed to a lab scale spray dryer whilst stirring at a feed rate of 5.7 ml/min and at a drying temperature of 75° C. (T out).

Figure 9:
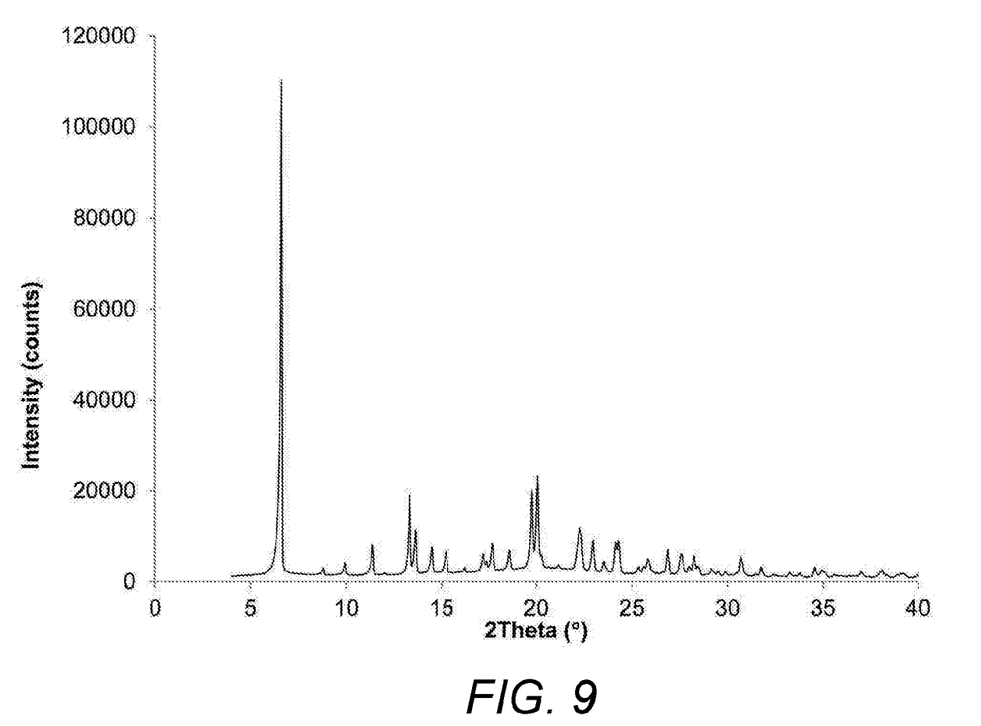
FIG. 9: XRPD umeclidinium bromide after high pressure homogenization micronization from Example 22.

The isolated product presented an XRPD identical to that of the starting material with a particle size distribution of Dv10=0.55 μm; Dv50=2.10 μm; Dv90=4.77 μm; span=2.03, as depicted in FIG. 9.

Instrument Parameters
NMR—Nuclear Magnetic Resonance $^1$H and $^{13}$C NMR spectra were recorded on a Bruker 300 Avance at 300 MHz ($^1$H-NMR) and 75 MHz ($^{13}$C-NMR).
MS—Mass Spectrometry MS experiments were performed on Micromass® Quattro Micro triple quadrupole (Waters®, Ireland) with an electrospray in positive ion mode (ESI+), ion source at 120° C., capillary voltage of 3.0 kV and source voltage of 30V.

HPLC—High Performance Liquid Chromatography

The HPLC analysis was conducted using a Waters® model Alliance/2695 and 2487 detector (dual λ) system under the following conditions:
Column: waters symmetry shield RP18 4.6×150 mm 3.5 micra
Flow rate: 0.8 mL/min
Injection Volume: 10 uL
Temperature: 30° C.
Solvents A: $H_2O$ (0.1% TFA)
Solvent B: $CH_3CN$
The gradient elution method as follows:

| Time (min.) | Flow (mL/min.) | Mobile phase A (%) | Mobile phase B (%) |
|---|---|---|---|
| 0.01 | 0.80 | 85.0 | 15.0 |
| 0.10 | 0.80 | 85.0 | 15.0 |
| 36.00 | 0.80 | 20.0 | 80.0 |
| 42.00 | 0.80 | 20.0 | 80.0 |
| 42.10 | 0.80 | 85.0 | 15.0 |
| 50.00 | 0.80 | 85.0 | 15.0 |

XRPD—X-ray Powder Diffraction

The X-ray powder patterns were recorded using the PANalytical X'Pert PRO X-ray diffraction system equipped with a copper source (Cu/Kα-1.54056 Å).
DSC—Differential Scanning Calorimetry DSC experiments were performed on DSC Q200, Ramp 10° C./min to 350° C.
TGA—Thermal Gravimetric Analysis TGA experiments were performed on TGA Q500, Ramp 10° C./min to 350° C.

The invention claimed is:

1. A process for preparing umeclidinium bromide comprising:
    a) reacting ethyl isonipecotate with 1-bromo-2-chloroethane in the presence of an organic base in a solvent to form ethyl 1-(2-chloroethyl)piperidine-4-carboxylate (II) or a salt thereof;
    b) reacting ethyl 1-(2-chloroethyl)piperidine-4-carboxylate (II) or a salt thereof with lithium diisopropylamide in a solvent to form ethyl 1-azabicyclo[2.2.2]octane-4-carboxylate (III);
    c) reacting ethyl 1-azabicyclo[2.2.2]octane-4-carboxylate (III) with phenyl lithium in a solvent to form 1-azabicyclo[2.2.2]oct-4-yl(diphenyl)methanol (IV); and
    d) reacting 1-azabicyclo[2.2.2]oct-4-yl(diphenyl)methanol (IV) with ((2-bromoethoxy)methyl) benzene in a solvent to form umeclidinium bromide,
    wherein the organic base in step a) is selected from the group consisting of 1,8-diazabicyclo [5.4.0]undec-7-ene, triethylamine, pyridine, N,N-diisopropylethyl amine, and 4-(dimethylamino)pyridine.

2. A process comprising:
    a) reacting ethyl isonipecotate with 1-bromo-2-chloroethane in the presence of organic base in a solvent to form ethyl 1-(2-chloroethyl)piperidine-4-carboxylate (II) or a salt thereof,
    wherein the organic base in step a) is selected from the group consisting of 1,8-diazabicyclo [5.4.0]undec-7-ene, triethylamine, pyridine, N,N-diisopropylethyl amine, and 4-(dimethylamino)pyridine.

3. The process according to claim 1, wherein the solvent in step a) comprises a ketone.

4. The process according to claim 1, wherein the salt formed in step a) is selected from the group consisting of hydrochloride, acetate, succinate, and oxalate.

5. The process according to claim 1, wherein the reaction of step a) is carried out at a temperature between about 20° C. and about 56° C.

6. The process according to claim 1, wherein step a) further comprises exchanging the solvent in step a) with an exchange solvent after the reacting and before performing step b).

7. The process according to claim 6, wherein the exchange solvent comprises one or more alkanes.

8. The process according to claim 1, wherein step a) further comprises performing an aqueous extraction after the reacting and before performing step b).

9. The process according to claim 8, wherein aqueous extraction comprises acidification with inorganic or organic acids.

10. The process according to claim 1, wherein step a) further comprises removing the dimer (diethyl 1,1'-(ethane-1,2-diyl)bis(piperidine-4-carboxylate) (V)) by filtration.

11. The process according to claim 10, wherein the reaction mixture is cooled prior to filtration.

12. The process according to claim 1, wherein the solvent in step (d) is selected from cyclic ethers, aromatic solvents, ketones and water.

13. The process according to claim 12, wherein the solvent is tetrahydrofuran, toluene or acetone.

14. The process according to claim 1, wherein the reaction of step d) is carried out at a temperature between about 40° C. and about 111° C.

15. The process according to claim 1, wherein after some of the umeclidinium bromide formed in step d) has precipitated from the reaction mixture, cooling down the reaction mixture to a temperature between about −10° C. and about 10° C., such that more of the umeclidinium bromide formed in step d) precipitates from the reaction mixture.

16. The process according to claim 1, wherein the process further comprises:
   e) recrystallizing umeclidinium bromide in a solvent.

17. The process according to claim 16, wherein the umeclidinium bromide is recrystallized from a solvent selected from a group consisting of alcohols, protic solvents and mixtures of both groups of solvents.

18. The process according to claim 1, wherein the process further comprises:
   f) micronizing the umeclidinium bromide.

19. The process according to claim 18, wherein the micronization is effected by cavitation and/or particle to particle collision and/or shear stress in the milling apparatus.

* * * * *